(12) United States Patent
DiGiore et al.

(10) Patent No.: US 9,775,983 B2
(45) Date of Patent: Oct. 3, 2017

(54) METHODS FOR MAKING AND USING IMPROVED LEADS FOR ELECTRICAL STIMULATION SYSTEMS

(71) Applicant: Boston Scientific Neuromodulation Corporation, Valencia, CA (US)

(72) Inventors: Andrew DiGiore, San Francisco, CA (US); John Michael Barker, Ventura, CA (US); Anne Margaret Pianca, Santa Monica, CA (US); Michael Adam Moffitt, Valencia, CA (US); Matthew Lee McDonald, Pasadena, CA (US); Joshua Dale Howard, Winnetka, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 105 days.

(21) Appl. No.: 14/722,029

(22) Filed: May 26, 2015

(65) Prior Publication Data

US 2015/0250999 A1 Sep. 10, 2015

Related U.S. Application Data

(62) Division of application No. 13/667,953, filed on Nov. 2, 2012, now Pat. No. 9,079,013.

(Continued)

(51) Int. Cl.
*H01R 43/00* (2006.01)
*A61N 1/05* (2006.01)

(52) U.S. Cl.
CPC .............. *A61N 1/05* (2013.01); *A61N 1/0534* (2013.01); *H01R 43/00* (2013.01);
(Continued)

(58) Field of Classification Search
CPC .......... A61K 9/70; A61N 1/05; A61N 1/0534; D01D 5/0015; D01D 5/34; Y10T 156/1062
See application file for complete search history.

(56) References Cited

U.S. PATENT DOCUMENTS 4,106,512 A    8/1978   Bisping
5,897,585 A    4/1999   Williams
(Continued)

OTHER PUBLICATIONS

International Search Report and Written Opinion dated Apr. 24, 2013 for International Application No. PCT/US2012/063351.
(Continued)

*Primary Examiner* — Minh Trinh
(74) *Attorney, Agent, or Firm* — Lowe Graham Jones PLLC; Bruce E. Black

(57) ABSTRACT

A method for manufacturing a lead includes pre-forming at least one relief section along a length of an elongated conductor having a first end and an opposing second end. The conductor with the pre-formed relief section is inserted into a conductor lumen defined along a length of an elongated lead body. The lead body has a first end and an opposing second end. An electrode is disposed at the first end of the lead body. The first end of the conductor is electrically coupled to the electrode. A terminal is disposed at the second end of the lead body. The second end of the conductor is electrically coupled to the terminal.

15 Claims, 9 Drawing Sheets

Related U.S. Application Data

(60) Provisional application No. 61/554,861, filed on Nov. 2, 2011.

(52) U.S. Cl.
CPC .... *Y10T 29/49174* (2015.01); *Y10T 29/49179* (2015.01); *Y10T 156/1062* (2015.01)

(56) References Cited

U.S. PATENT DOCUMENTS

| | | |
|---|---|---|
| 6,757,970 B1 | 7/2004 | Kuzma et al. |
| 7,809,446 B2 | 10/2010 | Meadows |
| 8,322,026 B2 | 12/2012 | McDonald |
| 8,473,061 B2 | 6/2013 | Moffitt et al. |
| 8,688,235 B1 | 4/2014 | Pianca et al. |
| 8,831,742 B2 | 9/2014 | Pianca et al. |
| 2006/0041293 A1 | 2/2006 | Mehdizadeh et al. |
| 2006/0252314 A1* | 11/2006 | Atalar ............ A61N 1/05 439/876 |
| 2007/0150036 A1 | 6/2007 | Anderson |
| 2009/0118610 A1 | 5/2009 | Karmarkar et al. |
| 2009/0187222 A1 | 7/2009 | Barker |
| 2009/0259282 A1 | 10/2009 | Williams et al. |
| 2009/0276021 A1 | 11/2009 | Meadows et al. |
| 2010/0076535 A1 | 3/2010 | Pianca et al. |
| 2010/0094364 A1* | 4/2010 | McDonald ............ A61N 1/05 607/2 |
| 2013/0105071 A1 | 5/2013 | DiGiore et al. |

OTHER PUBLICATIONS

Official Communication for U.S. Appl. No. 13/667,953 dated Oct. 8, 2014.

Official Communication for U.S. Appl. No. 13/667,953 dated Feb. 6, 2015.

* cited by examiner

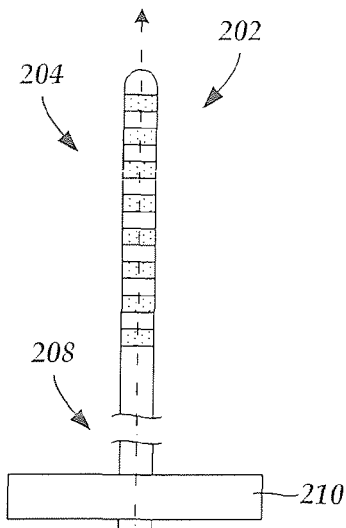
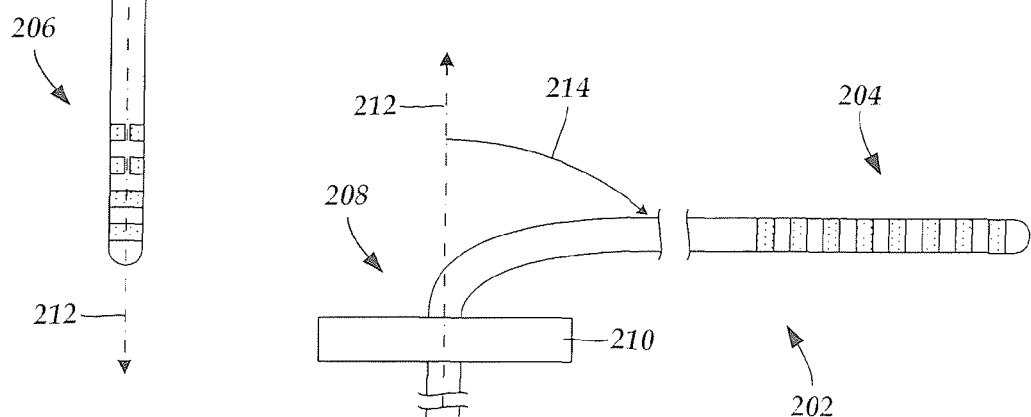
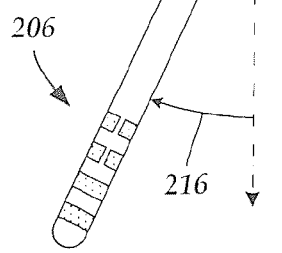

METHODS FOR MAKING AND USING IMPROVED LEADS FOR ELECTRICAL STIMULATION SYSTEMS

CROSS-REFERENCE TO RELATED APPLICATIONS

This application is a divisional of U.S. patent application Ser. No. 13/667,953 filed Nov. 2, 2012 which claims the benefit under 35 U.S.C. §119(e) of U.S. Provisional Patent Application Ser. No. 61/554,861 filed on Nov. 2, 2011, both of which are incorporated herein by reference.

FIELD

The invention is directed to the area of electrical stimulation systems and methods of making and using the systems. The present invention is also directed to electrical stimulation leads having leads with improved flexibility and strain relief, as well as methods of making and using the leads and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

In one embodiment, a method for manufacturing a lead includes pre-forming at least one relief section along a length of an elongated conductor having a first end and an opposing second end. The conductor with the pre-formed relief section is inserted into a conductor lumen defined along a length of an elongated lead body. The lead body has a first end and an opposing second end. An electrode is disposed at the first end of the lead body. The first end of the conductor is electrically coupled to the electrode. A terminal is disposed at the second end of the lead body. The second end of the conductor is electrically coupled to the terminal.

In another embodiment, a method for manufacturing a lead includes forming an access aperture in an elongated lead body having a first end and an opposing second end to expose a conductor lumen extending along a length of the lead body. A first end of an elongated conductor is inserted into the first end of the lumen and advanced along the conductor lumen until the first end of the conductor is visible through the access aperture from a location external to the lead body. The first end of the conductor is accessed through the access aperture and at least one relief section is formed along a portion of the conductor. The access aperture is sealed.

In yet another embodiment, a method for manufacturing a lead includes inserting an elongated conductor into a conductor lumen of an elongated first lead body portion having opposing first and second ends. A portion of the conductor that includes a first end of the conductor extends outwardly from the second end of the first lead body portion. A relief section is formed in the portion of the conductor extending outwardly from the second end of the first lead body portion. The first end of the conductor is inserted into a first end of a spacer section having opposing first and second ends until the first end of the spacer section abuts the second end of the first lead body portion and the relief section of the conductor is disposed in a strain relief cavity defined in the spacer section. When the first end of the spacer section abuts the second end of the first lead body portion, a portion of the conductor that includes the first end of the conductor extends outwardly from the second end of the spacer section. The first end of the conductor extending from the second end of the spacer section is inserted into a conductor lumen disposed at a first end of an elongated second lead body portion having opposing first and second ends until the first end of the second lead body portion abuts the second end of the spacer section. The first lead body portion, the second lead body portion, and the spacer section are reflowed to couple the spacer section to the first lead body portion and the second lead body portion.

In another embodiment, a method for manufacturing a lead includes inserting an elongated conductor into a conductor lumen of an elongated first lead body portion having opposing first and second ends. A portion of the conductor that includes a first end of the conductor extends outwardly from the second end of the first lead body portion. A relief section is formed in the portion of the conductor extending outwardly from the second end of the first lead body portion. A strain relief cavity is bored into a first end of an elongated second lead body portion having opposing first and second ends. The strain relief cavity is in communication with a conductor lumen extending along at least a portion of a longitudinal length of the second lead body portion. The first end of the conductor extending from the second end of the first lead body portion is inserted into the conductor lumen of the second lead body portion until the first end of the second lead body portion abuts the second end of the first lead body portion and the relief section of the conductor is disposed in the strain relief cavity defined in the second lead body portion. The first lead body portion and the second lead body portion are reflowed to couple the first lead body portion to the second lead body portion.

In yet another embodiment, a method for manufacturing a lead includes inserting a conductor into a conductor lumen defined along a length of an elongated lead body. The lead body has a first end and an opposing second end. The conductor is fixedly attached to the conductor lumen at a fixation attachment disposed along the length of the lead body. An electrode is disposed at the first end of the lead body. The first end of the conductor is electrically coupled to the electrode. A terminal is disposed at the second end of the lead body. The second end of the conductor is electrically coupled to the terminal.

In another embodiment, a method for manufacturing a lead includes inserting a conductor into a conductor lumen defined along a length of an elongated lead body. The lead body has a first end and an opposing second end. A first conductive contact is disposed at the first end of the lead body with a first gap formed between the first conductive contact and the first end of the lead body. The first end of the conductor is electrically coupled to the first conductive contact. A second conductive contact is disposed at the second end of the lead body. The second end of the conductor is electrically coupled to the second conductive contact. The first gap between the first conductive contact and the first end of the lead body is reduced. Reducing the first gap causes the conductor to form at least one first relief section.

In yet another embodiment, a method for manufacturing a lead includes inserting a conductor into a conductor lumen defined along a length of an elongated lead body. The lead body has a first end and an opposing second end. The lead body is stretched. An electrode is disposed at the first end of the lead body. The first end of the conductor is electrically coupled to the electrode. A terminal is disposed at the second end of the lead body. The second end of the conductor is electrically coupled to the terminal. The lead is allowed to relax. The relaxation of the lead body causes the conductor to form at least one relief section.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2A is a schematic side view of one embodiment of a intermediate portion of a lead being held in position by a retaining feature;

FIG. 2B is a schematic side view of one embodiment of a intermediate portion of the lead of FIG. 2A being held in position by the retaining feature of FIG. 2A and a proximal end of the lead being bent in a first direction, the bending of the proximal end causing a corresponding deflection of an opposing distal end of the lead in a second direction, opposite from the first direction;

DETAILED DESCRIPTION

The invention is directed to the area of electrical stimulation systems and methods of making and using the systems. The present invention is also directed to electrical stimulation leads having leads with improved flexibility and strain relief, as well as methods of making and using the leads and electrical stimulation systems.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Pat. No. 7,809,446 ("Devices and Methods For Brain Stimulation"). U.S. Patent Application Publication No. 2010/0076535 A1 ("Leads With Non-Circular-Shaped Distal Ends For Brain Stimulation Systems and Methods of Making and Using"), U.S. Patent Application Publication No. 2007/0150036 A1 ("Stimulator Leads and Methods For Lead Fabrication"). U.S. patent application Ser. No. 12/177,823 ("Lead With Transition and Methods of Manufacture and Use"). U.S. Patent Application Publication No. 2009/0276021 A1 ("Electrodes For Stimulation Leads and Methods of Manufacture and Use"). U.S. Patent Application Ser. No. 61/170,037 ("Deep Brain Stimulation Current Steering with Split Electrodes"), U.S. Patent Application Ser. No. 61/022,953, U.S. patent application Ser. No. 61/316,759, and U.S. Patent Application Publication No. 2009/0187222 A1. Each of these references is incorporated herein by reference in its respective entirety.

Figure 1:
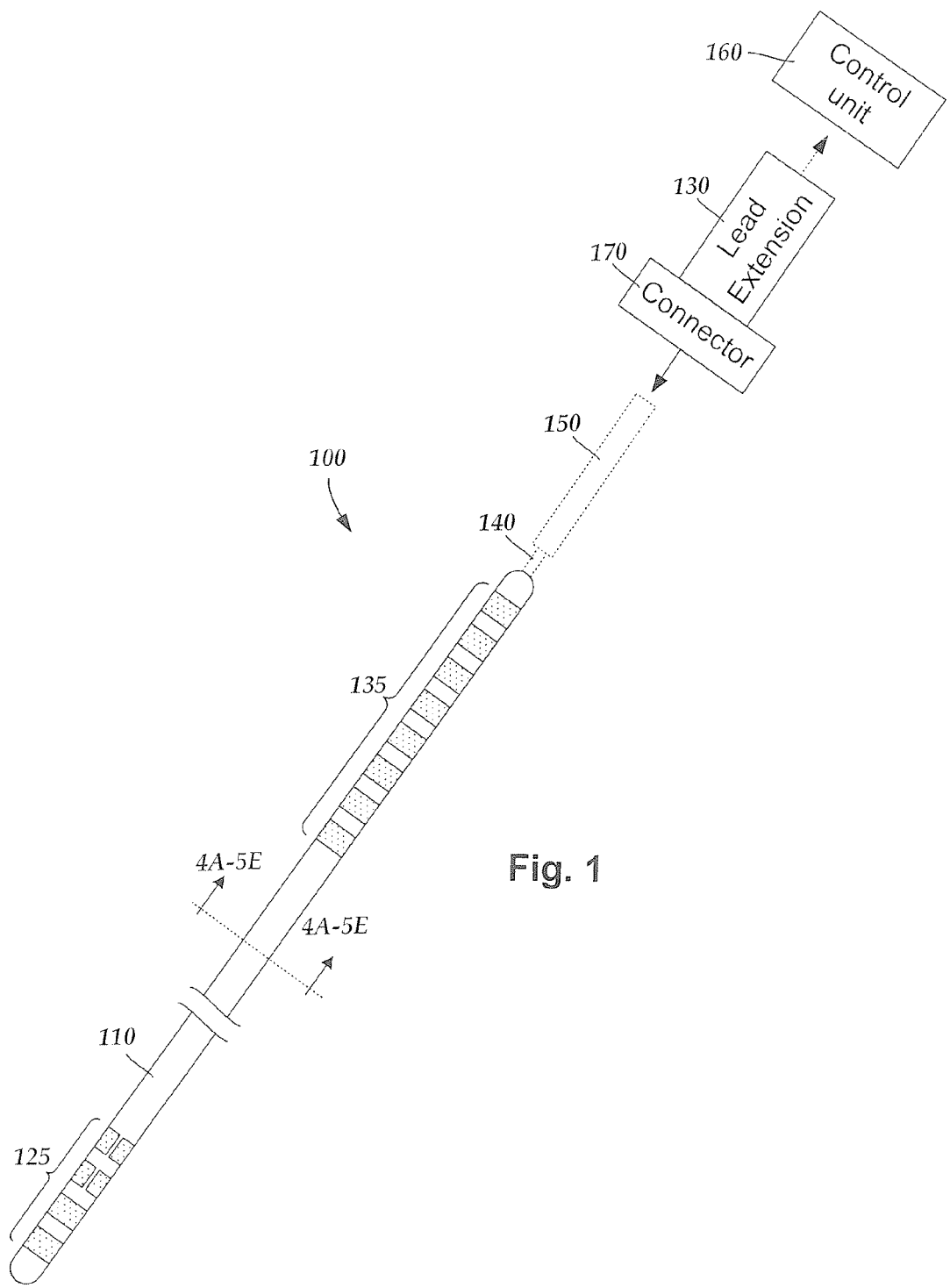
FIG. 1 is a schematic side view of one embodiment of a brain stimulation system that includes a lead, a lead extension, and a control unit, according to the invention.

FIG. 1 illustrates one embodiment of an electrical stimulation system 100 for brain stimulation. The electrical stimulation system 100 includes a lead 110, a plurality of electrodes 125 disposed at least partially about a circumference of the lead 110, a plurality of terminals 135, a lead extension 130 for connection of the electrodes 125 to a control unit 160, and a stylet 140 for assisting in insertion and positioning of the lead 110 in the patient's brain. It may be advantageous to include the lead extensions 130 to prevent having to remove or replace the lead 110 if the proximal end of the lead 110 fails due to fatigue (e.g., from flexing of the patient's neck, or the like).

The stylet 140 can be made of a rigid material. Examples of suitable materials include tungsten, stainless steel, or plastic. The stylet 140 may have a handle 150 to assist insertion into the lead 110, as well as rotation of the stylet 140 and lead 110. The lead extension 130 includes a connector 170 that fits over a proximal end of the lead 110, preferably after removal of the stylet 140.

The control unit 160 is typically an implantable pulse generator that can be implanted into a patient's body, for example, below the patient's clavicle area. The pulse generator can have eight stimulation channels which may be independently programmable to control the magnitude of the current stimulus from each channel. In some cases, the pulse generator may have more than eight stimulation channels (e.g., 16-, 32-, or more stimulation channels). The control unit 160 may have one, two, three, four, or more connector ports, for receiving the plurality of terminals 135 at the proximal end of the lead 110.

In one example of operation, access to the desired stimulation location in the brain can be accomplished by drilling a hole in the patient's skull or cranium with a cranial drill (commonly referred to as a "burr" or "bur"), and coagulating and incising the dura mater, or brain covering. The lead 110 can be inserted into the cranium and brain tissue with the assistance of the stylet 140. The lead 110 can be guided to the target stimulation location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 has a cross-sectional diameter of no more than 1.5 mm and may be in the range of 0.5 to 1.5 mm. In at least some embodiments, the lead 110 is rotatable so that the stimulation electrodes can be aligned with the target neurons after the neurons have been located using the recording electrodes. Stimulation electrodes may be disposed on the circumference of the lead 110 to stimulate the target neurons. Stimulation electrodes may be ring-shaped or segmented.

The lead extension 130 typically couples the electrodes 125 to the control unit 160 (which typically houses a pulse generator that supplies electrical signals to the electrodes 125). Connectors of conventional lead extensions are typically disposed within patient tissue such that the connectors are disposed over the patient's skull and beneath or within the patient's scalp above one of the patient's ear.

It may be desirable for a lead to be flexible. As discussed above, during implantation a distal end of the lead is typically inserted into a burr hole in the patient's scalp and positioned such that the electrodes are disposed at a target stimulation location (e.g., the sub thalamic nucleus, the globus pallidus interna, the ventral intermediate nucleus, or the like). A proximal end of the lead is typically coupled to a connector of a lead extension or control unit. In which case, the lead may make an approximately 90° bend in proximity to an outer portion of the burr hole through which the distal end of the lead is extended. Consequently, it may be desirable for the lead to be flexible enough to be able to make such a bend.

Bending one portion of the lead, however, might cause a corresponding undesired deflection at another portion of the lead. For example, bending in a proximal portion or an intermediate portion of the lead may cause a corresponding undesired deflection at a distal end of the lead. Such a deflection may be caused, at least in part, by one or more conductors of the lead being held in tension, while one or more other conductors of the lead are held in compression.

FIG. 2A is a schematic side view of one embodiment of a lead 202 having a proximal portion 204, a distal portion 206, and an intermediate portion 208. The intermediate portion 208 of the lead 202 is held in position by a retaining feature 210 (e.g., a burr hole plug or cap, bone cement, one or more mini-plates, or the like). An axis 212 is shown passing through the portion of the lead 202 extending through the retaining feature 210. In FIG. 2A, the lead 202 is shown in a straight configuration, such that the entire lead 202 extends along the axis 212.

FIG. 2B is a schematic side view of one embodiment of the proximal portion 204 of the lead 202 bent in a first direction, away from the axis 212, as shown by arrow 214. As shown in FIG. 2B, bending of the proximal portion 204 of the lead 202 in a first direction causes a corresponding deflection of the distal portion 206 of the lead 202 in a second direction, away from the axis 212, as shown by arrow 216.

Accordingly, it may be desirable for the lead to include strain relief that reduces or prevents the bending of the lead proximal to a retaining feature (e.g., a burr hole plug or cap, bone cement, one or more mini-plates, or the like) from causing a corresponding deflection of the lead distal to the retaining feature. As herein described, the lead includes strain relief that reduces, or even prevents, bending of a first portion of the lead from causing a corresponding deflection of a second portion of the lead.

Figure 3:
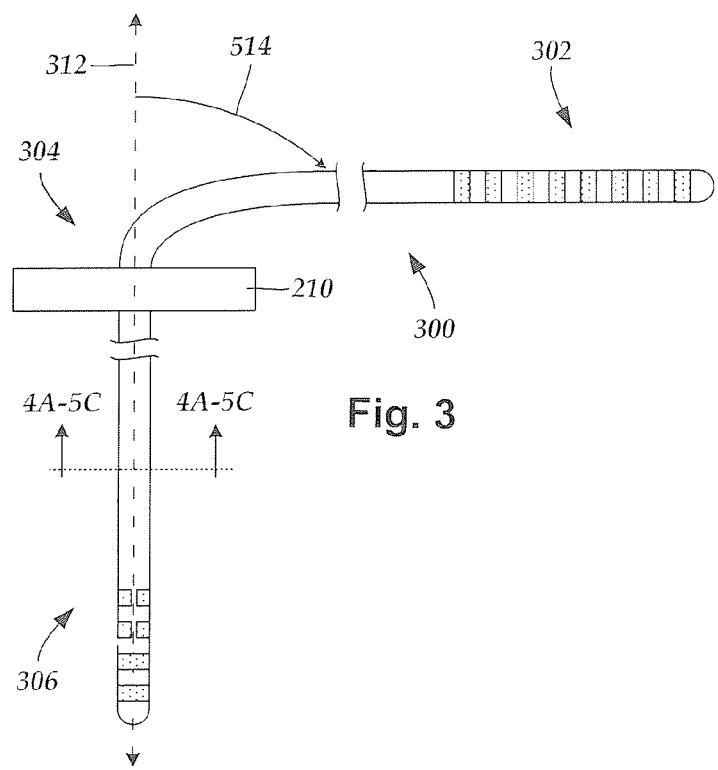
FIG. 3 is a schematic side view of one embodiment of a intermediate portion of a lead held in position by the retaining feature of FIG. 2A and a proximal end of the lead being bent in a first direction, the bending of the proximal end not causing any corresponding deflections of an opposing distal end of the lead, according to the invention.

FIG. 3 is a schematic side view of one embodiment of a lead 300. The lead 300 has a proximal portion 302, an intermediate portion 304, and a distal portion 306. The intermediate portion 304 is held in a relatively stationary position by the retaining feature 210 (e.g., a burr hole plug or cap, bone cement, one or more mini-plates, or the like). An axis 312 is shown passing through the portion of the lead 300 extending through the retaining feature 210.

In FIG. 3, a portion of the lead 300 is shown bent in a first direction from the axis 312, as shown by arrow 314. It will be understood that the bend may occur at any suitable location along the length of the lead 300. For example, in some cases the bend may occur distal to the terminals and proximal to the electrodes. As shown in FIG. 3, bending of a portion of the lead 300 in a first direction does not cause a corresponding deflection of the distal portion 306 of the lead 300.

Strain relief may be provided in any suitable manner. In some embodiments, the lead includes a lead body with an elongated multi-lumen conductor guide. In which case, the multi-lumen conductor guide may include conductor lumens with one or more helical sections that provide strain relief. In some embodiments, strain relief may be provided by increasing the amount of clearance between the conductors and the conductor lumens within which the conductors extend. Strain relief may, optionally, be provided by coating insulation disposed around the conductors with one or more materials that reduce the coefficient of friction between the conductors and the conductor lumens within which the conductors extend, thereby increasing the ability of the conductors to slide relative to the conductor lumens within which the conductors extend.

In at least some embodiments, strain relief may be provided by one or more relief sections disposed along a length of one or more of the conductors of the lead. As herein described, a relief section of a conductor is a section of the conductor that includes one or more curved structures that are repeating or quasi-repeating in form. The one or more curved structures of the relief section can include any suitable configurations including, for example, one or more coils, bends, zigzags, crimps, arches, sinusoids, hooks, wiggles, squiggles, arcs, curls, rings, ringlets, waves, undulations, serpentines, loops, jumbles, knots, overlapping regions, or the like or combinations thereof.

The structures can have any suitable pitch. The pitch of the structures can be either uniform or non-uniform. Any suitable number of relief sections can be disposed on one or more of any suitable number of conductors of the lead including, for example, one, two, three, four, five, six, seven, eight, nine, ten, eleven, twelve or more relief sections. When a plurality of relief sections are disposed along the conductor, the relief sections may be axially-spaced-apart from one another along a longitudinal length of the conductor. The relief sections can be any suitable width or length. When a plurality of relief sections are disposed on the conductor, in at least some embodiments at least one of the plurality of relief sections has a length or width or both that is different from at least one other of the plurality of relief sections. The one or more conductors on which the one or more relief sections are disposed can be either single filar or multi-filar.

In some embodiments, one or more of the conductors are pre-formed with one or more relief sections prior to insertion of the conductors into the lead body. In other cases, strain relief may be provided by forming one or more relief sections along the conductors during, or after, insertion of the conductors into the lead body.

In some embodiments, strain relief may be provided by disposing one or more relief sections of conductors within strain relief cavities in communication with conductor lumens. The strain relief cavities may be defined along one or more portions of the lead body, or in one or more spacer sections disposed along a length of the lead body, or both. Strain relief may, optionally, be provided by forming one or more fixed attachments between the conductors and the lumens within which the conductors extend at one or more locations along the length of the lead body.

In some embodiments, strain relief may be provided by coupling conductors to electrodes and terminals disposed at the ends of the lead body with gaps formed at one (or both) of the ends of the lead body, then pushing one (or both) of the ends of the lead together to reduce (or eliminate) the gap(s), thereby forming one or more relief sections along the conductors within lead body. In some embodiments, strain relief may be provided by inserting the conductors into the lead body and electrically coupling the conductors to electrodes and terminals while the lead body is stretched along a longitudinal length of the lead body, then allowing the lead body to relax, thereby forming one or more relief sections along the conductors within lead body. It will be understood that any of the above techniques for providing strain relief can be used in any suitable combination with each other for providing strain relief.

Figure 4A:
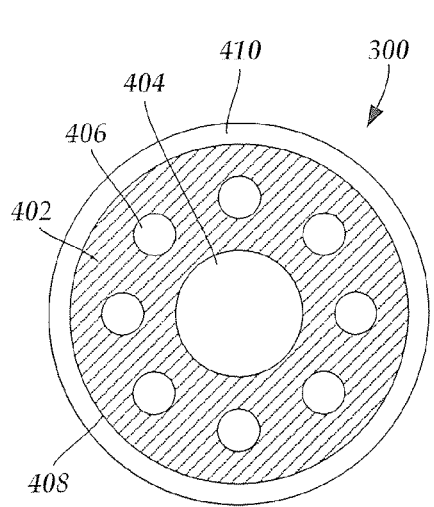
FIG. 4A is a transverse cross-sectional view of one embodiment of the lead of FIG. 3, the lead including a multi-lumen conductor guide that defines a central lumen and a plurality of conductor lumens arranged around the central lumen, according to the invention.

Turning to FIG. 4A, in at least some embodiments, the lead includes a lead body with an elongated multi-lumen conductor guide having multiple conductor lumens arranged about a central lumen. In at least some embodiments, the conductor lumens are arranged about the central lumen such that there are no other lumens extending along the multi-lumen conductor guide between the central lumen and each of the multiple conductor lumens. The conductor lumens include at least one helical section forming an enclosed pathway around at least a portion of the central lumen. In some embodiments, the conductor lumens are each configured and arranged to receive a single conductor. In other embodiments, at least one of the conductor lumens is configured and arranged to receive multiple conductors.

FIG. 4A is a transverse cross-sectional view of one embodiment of the lead 300. The lead 300 includes an elongated multi-lumen conductor guide 402. The multi-lumen conductor guide 402 may extend an entire longitudinal length of the lead 300 from the electrodes 125 to the terminals 135. As shown in FIG. 4A, the multi-lumen conductor guide 402 defines a central lumen 404 and a plurality of conductor lumens, such as conductor lumen 406. The conductor lumens can have any suitable cross-sectional shape (e.g., round, oval, rectangular, triangular, or the like).

In at least some embodiments, the plurality of conductor lumens 406 are encapsulated by the multi-lumen conductor guide 402 such that the conductor lumens 406 do not extend to an outer surface 408 of the multi-lumen conductor guide 402. In which case, when conductors (420 in FIG. 4B) are disposed in the conductor lumens 406, the conductors are not exposed along the outer surface 408 of the multi-lumen conductor guide 402. The central lumen 404 and the plurality of conductor lumens 406 can be arranged in any suitable manner. In preferred embodiments, the conductor lumens 406 are disposed in the multi-lumen conductor guide 402 such that the conductor lumens 406 are peripheral to the central lumen 404. In at least some embodiments, the lead 300 may include one or more outer coatings of material 410 disposed over the outer surface 408 of multi-lumen conductor guide 402.

Figure 4B:
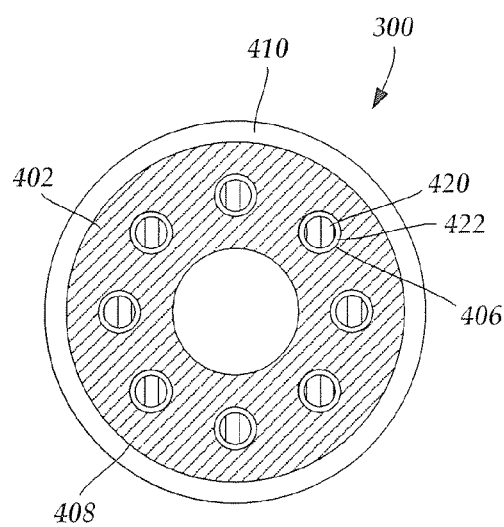
FIG. 4B is a transverse cross-sectional view of one embodiment of conductors disposed in each of a plurality of conductor lumens of the multi-lumen conductor guide of FIG. 4A such that a different single conductor is disposed in each of the conductor lumens, according to the invention.

The central lumen 404 may be configured and arranged to receive a stylet, such as the stylet (140 in FIG. 1). As discussed above, the stylet 140 can be used for assisting in insertion and positioning of the lead 300 in the patient's brain. The plurality of conductor lumens 406 are configured and arranged to receive conductors, which electrically couple the electrodes 125 to the terminals 135. FIG. 4B is a transverse cross-sectional view of one embodiment of conductors, such as conductor 420, disposed in the conductor lumens 406. In at least some embodiments, insulation 422 is disposed around the conductors 420 to prevent short-circuiting of the conductors 420.

Figure 5A:
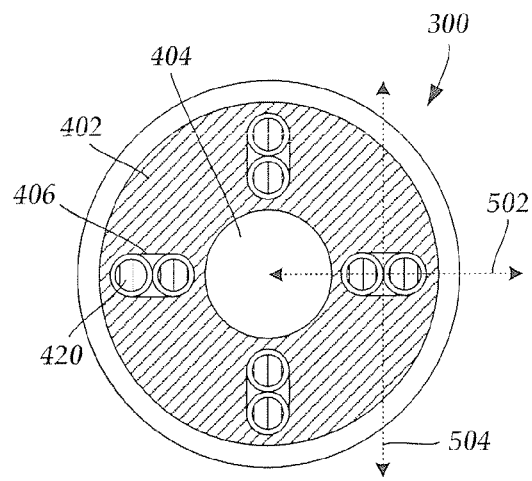
FIG. 5A is a transverse cross-sectional view of another embodiment of the multi-lumen conductor guide of FIG. 4A, the multi-lumen conductor guide defining a plurality of conductor lumens, each of the plurality of conductor lumens receiving a plurality of conductors, according to the invention.
Figure 5B:
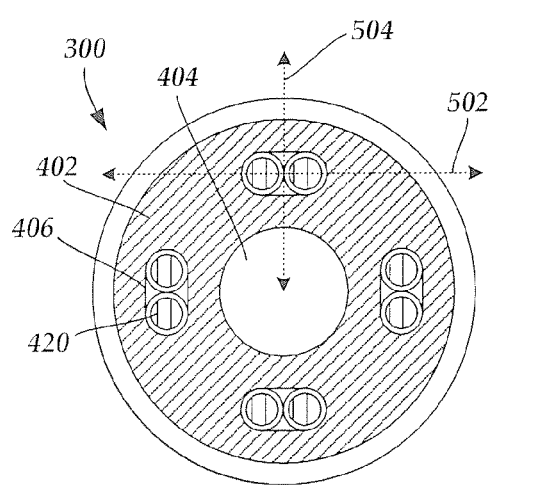
FIG. 5B is a transverse cross-sectional view of yet another embodiment of the multi-lumen conductor guide of FIG. 4A, the multi-lumen conductor guide defining a plurality of conductor lumens, each of the plurality of conductor lumens receiving a plurality of conductors, according to the invention.
Figure 5C:
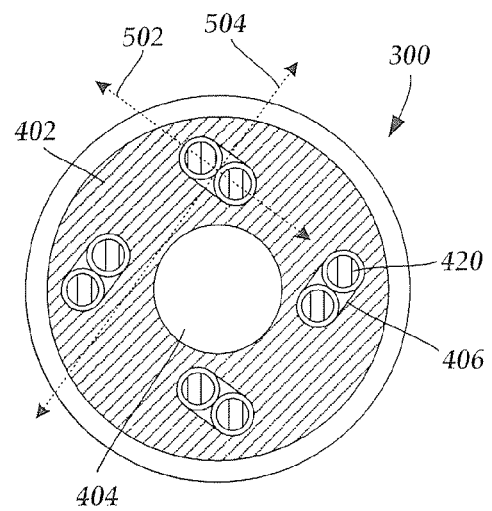
FIG. 5C is a transverse cross-sectional view of another embodiment of the multi-lumen conductor guide of FIG. 4A, the multi-lumen conductor guide defining a plurality of conductor lumens, each of the plurality of conductor lumens receiving a plurality of conductors, according to the invention.

In some cases, two or more conductors 420 can be disposed in one or more of the conductor lumens 406. In at least some cases, the multi-lumen conductor guide 402 defines more than one conductor lumen 406, yet includes fewer conductor lumens 406 than conductors 420. FIG. 5A-5C are transverse cross-sectional views of three other embodiments of the multi-lumen conductor guide 402 defining the central lumen 404 and a plurality of conductor lumens, such as conductor lumen 406, where the number of conductor lumens 406 is less than the number of conductors 420. Any suitable such configuration can be implemented. In FIGS. 5A-5C, the multi-lumen conductor guide 402 includes four conductor lumens 406 and eight conductors 420. Each of the conductor lumens shown in FIG. 5A-5C are configured and arranged to receive two conductors 420. In other embodiments, at least one of the conductor lumens 406 can be configured and arranged to receive a different number of conductors than at least one other of the conductor lumens 406.

When the conductor lumens 406 are configured and arranged to receive a plurality of conductors, the conductor lumens 406 can be arranged in any suitable configuration. In FIGS. 5A-5C, the conductor lumens 406 each have a major axis 502 and a minor axis 504 that is perpendicular to the major axis 502. In FIG. 5A, the conductor lumens 406 are configured and arranged such that the major axes 502 of the conductor lumens 406 extends radially outward from the central lumen 404. In FIG. 5B, the conductor lumens 406 are configured and arranged such that the minor axes 504 of the conductor lumens 406 extends radially outward from the central lumen 404. In FIG. 5C, the conductor lumens 406 are configured and arranged such that neither the major axes 502 nor the minor axis 504 of the conductor lumens 406 extend radially outward from the central lumen 404.

Figure 6A:
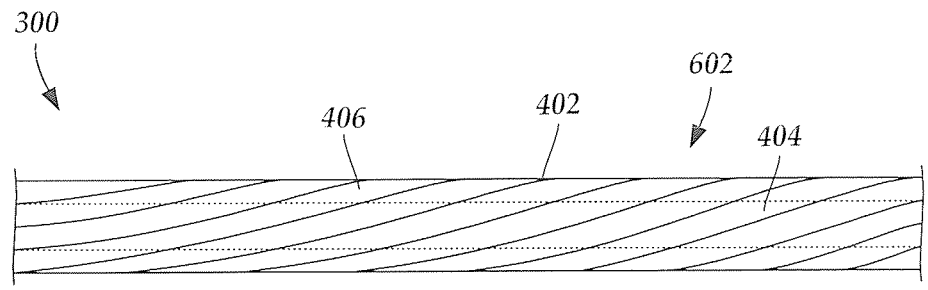
FIG. 6A is a schematic side view of one embodiment of a helical section of the multi-lumen conductor guide of FIG. 4A, the helical section defining a plurality of conductor lumens each defining a clockwise helical pathway around at least a portion of a central lumen, according to the invention.
Figure 6B:
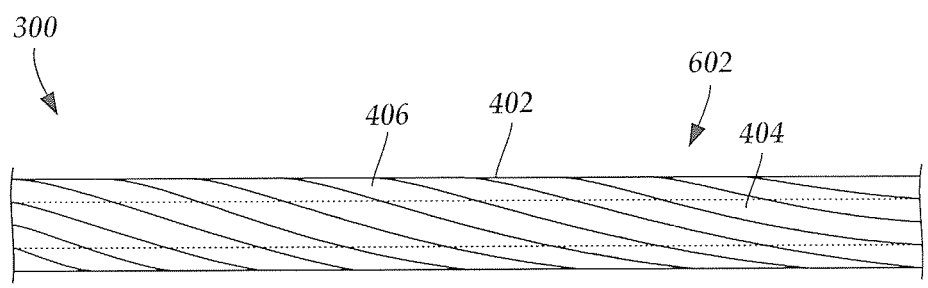
FIG. 6B is a schematic side view of another embodiment of a helical section of the multi-lumen conductor guide of FIG. 4A, the helical section defining a plurality of conductor lumens each defining a counter-clockwise helical pathway around at least a portion of a central lumen, according to the invention.

In some embodiments, the lead includes a lead body with an elongated multi-lumen conductor guide. In which case, the multi-lumen conductor guide may include conductor lumens with one or more helical sections that provide strain relief. FIGS. 6A and 6B are schematic side views of two embodiments of a helical section 602 of the multi-lumen conductor guide 402. The helical section 602 can extend an entire length of the multi-lumen conductor guide 402, or one or more portions thereof. The multi-lumen conductor guide 402 defines a plurality of conductor lumens, such as conductor lumen 406, twisted such that the individual conductor lumens 406 form helical pathways around the central lumen 404. The conductor lumens 406 can extend in either clockwise or counter-clockwise directions. In FIG. 6A, the conductor lumens 406 are shown extending in a clockwise direction around to the central lumen 404 (e.g., the conductor lumens 406 wrap around the central lumen in a clockwise direction when the multi-lumen conductor guide 402 is viewed from the distal end). In FIG. 6B, the conductor lumens 406 are shown extending in a counter-clockwise direction around to the central lumen 404 (e.g., the conductor lumens 406 wrap around the central lumen in a counter-clockwise direction when the multi-lumen conductor guide 402 is viewed from the distal end). It should be understood that the twisted lead embodiments of FIGS. 6A and 6B may have transverse, cross-sections that are shown in FIGS. 4A, 4B, 5A, 5B and 5C.

The conductor lumens 406 of the helical section 602 can be any suitable pitch. The pitch can be either constant or variable. In some cases, the pitch may be at least 0.04 turns (i.e., 0.04 revolutions around a circumference of the central lumen 404) per cm. In some cases, the pitch may be no less than 0.1 turns per cm. In some cases, the pitch may be at least 0.2 turns per cm. In some cases, the pitch may be at least 0.25 turns per cm. In some cases, the pitch may be at least 0.8 turns per cm.

In some cases, the pitch may be at least 0.04 turns per cm and no greater than 0.8 turns per cm. In some cases, the pitch may be at least 0.1 turns per cm and no greater than 0.6 turns per cm. In some cases, the pitch may be at least 0.1 turns per cm and no greater than 0.4 turns per cm. In some cases, the pitch may be at least 0.2 turns per cm and no greater than 0.4 turns per cm. In some cases, the pitch may be approximately 0.3 turns per cm.

In some cases, for a 40 cm section of the multi-lumen conductor guide 402, each conductor lumen 406 of the helical section 602 forms at least 2, 3, 4, or 5 turns. In some cases, for a 40 cm section of the multi-lumen conductor guide 402, each conductor lumen 406 of the helical section 602 forms no more than 25 turns.

In some cases, for a 40 cm section of the multi-lumen conductor guide 402, each conductor lumen 406 of the helical section 602 forms at least 2 turns and no more than 15 turns. In some cases, for a 40 cm section of the multi-lumen conductor guide 402, each conductor lumen 406 of the helical section 602 forms no less than 3 turns and no more than 15 turns. In some cases, for a 40 cm section of the multi-lumen conductor guide 402, each conductor lumen 406 of the helical section 602 forms at least 4 turns and no more than 15 turns. In some cases, for a 40 cm section of the multi-lumen conductor guide 402, each conductor lumen 406 of the helical section 602 forms at least 5 turns and no more than 15 turns.

The conductor lumens 406 of the helical section 602 can be configured into any suitable arrangement (see e.g., FIGS. 4A-5C). The helical section 602 may include a single layer of conductor lumens 406 disposed over the central lumen 404. The conductor lumens 406 may be disposed over a single central lumen 404. In some cases, a single layer of conductor lumens 406 is disposed over a single central lumen 404.

In some cases, the helical section 602 extends along an entire length of the lead 300 between the electrodes (125 in FIG. 1) and the terminals (135 in FIG. 1). In other cases, the helical section 602 extends along one or more discrete sections of the lead 300. When the helical section 602 extends along one or more discrete sections of the lead 300, the discrete helical section 602 can be any suitable length. In some cases, the discrete helical section 602 is at least 1 cm, 2 cm, 3 cm, 4 cm, 5 cm, 6 cm, 7 cm, 8 cm, 9 cm, 10 cm, 15 cm, 20 cm, 25 cm, 30 cm, or longer.

Figure 7A:
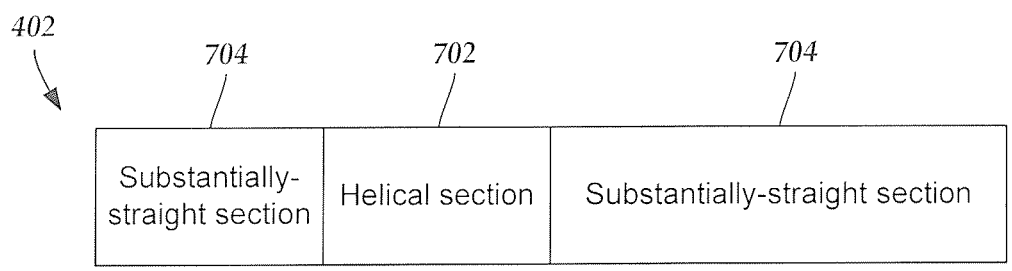
FIG. 7A is a schematic side view of one embodiment of a portion of the multi-lumen conductor guide of FIG. 4A, the portion of the multi-lumen conductor guide defining the discrete helical section of either FIG. 6A or FIG. 6B, according to the invention.

Turning to FIG. 7A, when the helical section 602 extends along a discrete section of the multi-lumen conductor guide 402, the discrete helical section 602 can be disposed at any suitable location along the length of the lead 300. In some cases, the discrete helical section 300 may abut the electrodes (125 in FIG. 1), the terminals (135 in FIG. 1), or both. In other cases, the discrete helical section 602 can be disposed somewhere along the length of the lead 300 between the electrodes (125 in FIG. 1) and the terminals (135 in FIG. 1). When the discrete helical section 602 is disposed somewhere along the length of the lead 300 between the electrodes (125 in FIG. 1) and the terminals (135 in FIG. 1), the remaining portions of the conductor lumens 406 can be arranged into one or more other configurations, such as a substantially-straight configuration (e.g., the conductor lumens 406 extend less than one revolution about a circumference of the central lumen 404 along a 20 cm length of the multi-lumen conductor guide 402).

FIG. 7A is a schematic side view of one embodiment of a portion of the multi-lumen conductor guide 402. The portion of the multi-lumen conductor guide 402 defines a discrete helical section 702 where each of a plurality of conductor lumens defines a helical pathway around at least a portion of a circumference of a central lumen. In FIG. 7A, substantially-straight sections 704 of the conductor lumens extend along the multi-lumen conductor guide 402 on either end of the discrete helical section 702. The helical section 702 and the flanking substantially-straight sections 704 can be any suitable lengths relative to one another.

Figure 7B:
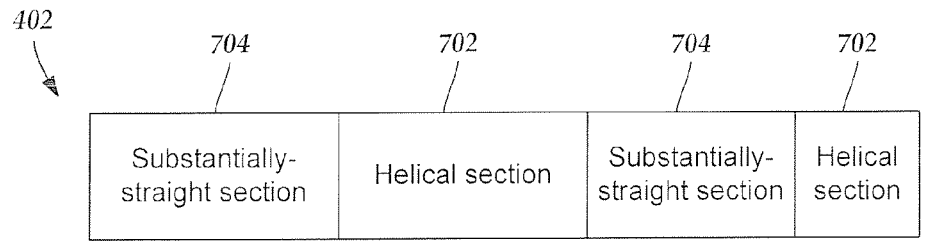
FIG. 7B is a schematic side view of one embodiment of a portion of the multi-lumen conductor guide of FIG. 4A, the portion of the multi-lumen conductor guide defining a plurality of the discrete helical sections of either FIG. 6A or FIG. 6B each separated from one another by substantially-straight sections, according to the invention.

Turning to FIG. 7B, in some cases the multi-lumen conductor guide includes a plurality of helical sections. When the lead includes a plurality of helical sections, the conductor lumens of the helical sections can extend around the central lumen in either: a clockwise direction; a counter-clockwise direction; or a combination of both, where at least one conductor lumen extends clockwise and at least one conductor lumen that extends counter-clockwise around the circumference of the central lumen. In some cases, when the multi-lumen conductor guide includes a plurality of helical sections, the helical sections each have equal lengths. In other cases, when the lead includes a plurality of helical sections, at least one of the helical sections has a length that is different from at least one other of the plurality of helical sections.

FIG. 7B is a schematic side view of one embodiment of a portion of the multi-lumen conductor guide 402. The portion of the multi-lumen conductor guide 402 defines a plurality of the discrete helical sections 702. In FIG. 7B, a substantially-straight section 704 is disposed between the discrete helical sections 702.

Figure 7C:
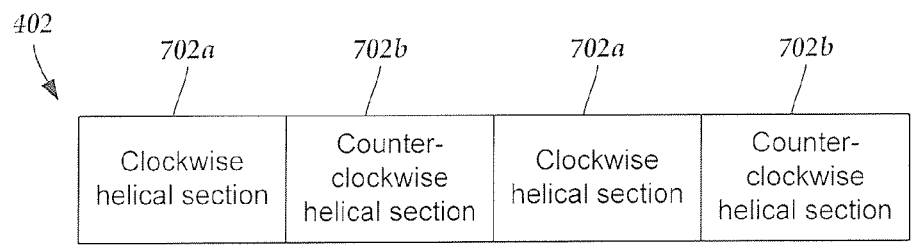
FIG. 7C is a schematic side view of one embodiment of a portion of the multi-lumen conductor guide of FIG. 4A, the portion of the multi-lumen conductor guide defining a plurality of the discrete helical sections of FIG. 6A and FIG. 6B abutting one another, according to the invention.

Turning to FIG. 7C, in some cases the multi-lumen conductor includes two abutting discrete helical sections with conductors winding in opposite directions. FIG. 7C is a schematic side view of one embodiment of a portion of the multi-lumen conductor guide 402. The portion of the multi-lumen conductor guide 402 defines a plurality of the discrete helical sections abutting one another. At least one of the helical sections 702a includes conductor lumens arranged in a clockwise configuration, and at least one of the helical sections 702b includes conductor lumens arranged in a counter-clockwise configuration.

Figure 7D:
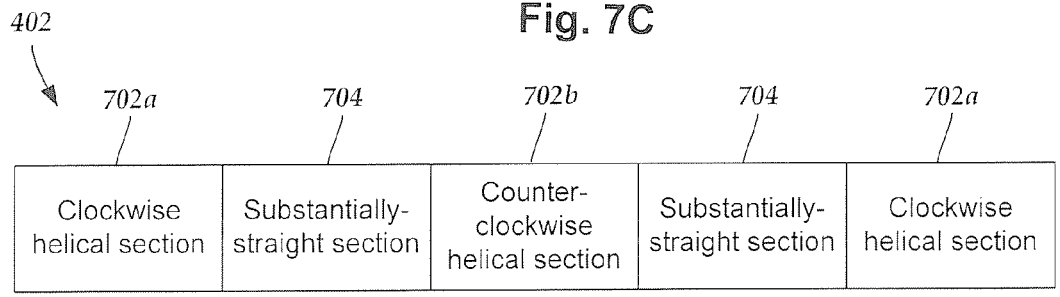
FIG. 7D is a schematic side view of one embodiment of a portion of the multi-lumen conductor guide of FIG. 4A, the portion of the multi-lumen conductor guide defining a plurality of the discrete helical sections of FIG. 6A and FIG. 6B with alternating winding geometries, the helical sections each separated from one another by substantially-straight sections, according to the invention.

Turning to FIG. 7D, in some cases the multi-lumen conductor includes multiple discrete helical sections with conductors winding in opposite directions, where the discrete helical sections are separated from one another by substantially-straight sections. FIG. 7D is a schematic side view of one embodiment of a portion of the multi-lumen conductor guide 402. The portion of the multi-lumen conductor guide 402 defines a plurality of discrete helical sections 702a and 702b. The helical sections alternate between helical sections 702a having conductor lumens arranged in a clockwise configuration, and helical sections 702b having conductor lumens arranged in a counter-clockwise configuration. A substantially-straight section 704 separates each of the alternating helical sections 702a and 702b from one another.

Figure 7E:
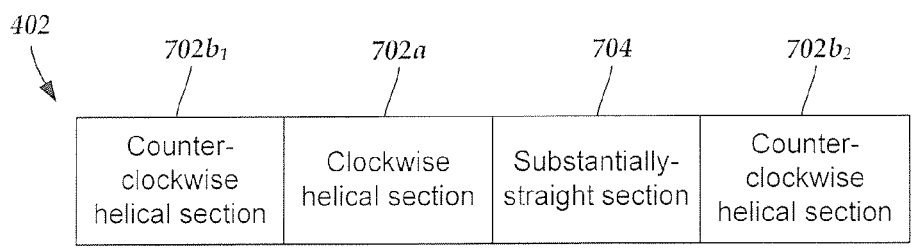
FIG. 7E is a schematic side view of one embodiment of a portion of the multi-lumen conductor guide of FIG. 4A, the portion of the multi-lumen conductor guide defining a plurality of the discrete helical sections of FIG. 6A and FIG. 6B, some of the helical sections abutting one another and some of the helical sections separated from one another by a substantially-straight section, according to the invention.

FIG. 7E is a schematic side view of one embodiment of a portion of the multi-lumen conductor guide 402. The portion of the multi-lumen conductor guide 402 defines a plurality of discrete helical sections. At least some of the helical sections, such as helical sections 702a and 702$b_1$, abut one another. At least some of the helical sections, such as helical sections 702a and 702$b_2$, are separated from one another by a substantially-straight section 704. Additionally, at least one of the helical sections, such as helical section 702a includes conductor lumens arranged in a clockwise configuration, and at least one of the helical sections, such as helical sections 702$b_1$ and 702$b_2$, include conductor lumens arranged in a counter-clockwise configuration.

The multi-lumen conductor guide 402 can be formed as a single-piece component or as a multi-piece component. The multi-lumen conductor guide 402 can be formed from any suitable material(s). For example, the multi-lumen conductor guide 402 can be formed from one or more thermoset polymers, thermoplastic polymers (e.g., polyurethane, or the like), silicone, or the like or combinations thereof.

The multi-lumen conductor guide 402 can be formed in any suitable manner. For example, the multi-lumen conductor guide 402 can be extruded. In some cases, the multi-lumen conductor guide 402 can be twisted as the multi-lumen conductor guide 402 is being extruded, or after extrusion.

The multi-lumen conductor guide 402 can be formed such that the conductor lumens are in substantially-straight configurations. In some cases, the multi-lumen conductor guide 402 (or one or more portions thereof) with the substantially-straight conductor-lumen configurations can be twisted, as desired, to form one or more helical sections. Once the twisting is complete, the twisted multi-lumen conductor guide can be heated to set the helical section(s). In other cases, the multi-lumen conductor guide can be heated prior to twisting. In yet other cases, the multi-lumen conductor guide can be heated while being twisted. The heating can be performed using at least one of: one or more transverse heating elements which heat one or more particular portions of the multi-lumen conductor guide at a time, or an elongated heating element that heats the entire multi-lumen conductor guide at once. In some cases, the lead can be heated from the inside out, for example, by using one or more heating elements disposed in the central lumen.

In some cases, the conductors can be disposed in the conductor lumens prior to heating. In other cases, the conductor lumens can be empty during heating. In at least some embodiments, one or more mandrels are disposed in the central lumen 404. In at least some alternate embodiments, one or more mandrels are disposed in one or more of the conductor lumens. In which case, it may be advantageous to dispose the mandrels in the conductor lumens prior to heating of the multi-lumen conductor guide to prevent the conductor lumens from collapsing during heating.

When one or more mandrels are disposed in one or more conductor lumens, in at least some cases a different mandrel is disposed in each of the conductor lumens during the heating process and then removed for insertion of the conductors. The mandrels disposed in the conductor lumens can have any suitable diameter. In at least some cases, the mandrels have diameters that are smaller than diameters of the conductor lumens, yet larger than diameters of the conductors. It may be advantageous to use mandrels with diameters that are smaller than diameters of the conductor lumens, yet larger than diameters of the conductors so that, during the heating process, the conductor lumens do not shrink to a size that prevents (or makes difficult) insertion of the conductors into the conductor lumens after the multi-lumen conductor guide is twisted and heated, and the mandrels are removed.

Figure 8A:
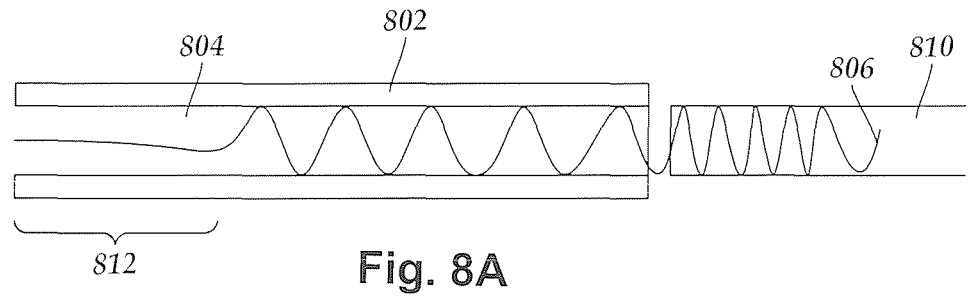
FIG. 8A is a schematic longitudinal cross-sectional view of one embodiment of a portion of a lead defining a lumen within which a conductor extends, the conductor having a pre-formed wave, according to the invention.

Turning to FIG. 8A, in some cases strain relief is provided by using conductors with one or more relief sections. The relief sections may provide strain relief for the conductors when the lead body is bent, twisted, stretched, or the like (see e.g., FIG. 2A). In at least some embodiments, one or more relief sections are formed along the one or more conductors prior to insertion of the conductors into the lead body.

Figure 8B:
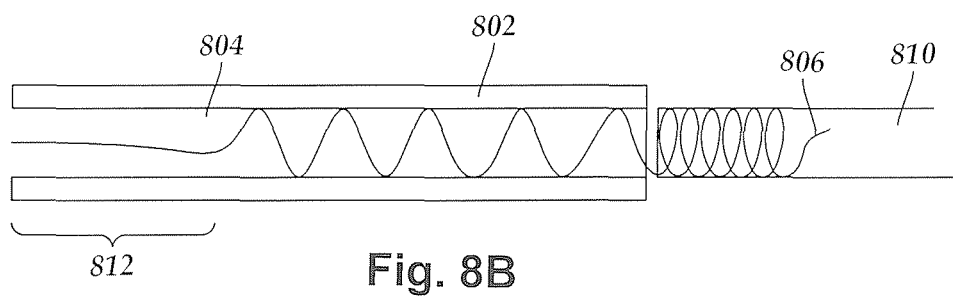
FIG. 8B is a schematic longitudinal cross-sectional view of one embodiment of a portion of a lead defining a lumen within which a conductor extends, the conductor having a pre-formed coil, according to the invention.

FIGS. 8A and 8B are schematic longitudinal cross-sectional views of two embodiments of a portion of a lead body 802. The portion of the lead body 802 defines a conductor lumen 804 within which a conductor 806 is disposed. The conductor 806 includes one or more pre-formed relief sections. In FIG. 8A, the conductor 806 includes a plurality of axially-spaced-apart pre-formed waves extending along a longitudinal length of the conductor 806. In FIG. 8B, the conductor 806 includes a plurality of axially-spaced-apart pre-formed coils extending along a longitudinal length of the conductor 806.

The conductors 806 with the pre-formed relief sections can be inserted into the conductor lumens 804 in any suitable manner. In some cases, the conductor 806 can be pulled through the conductor lumen 804 using a pull mandrel 810, or the like, attached to one end of the conductor 806. In other cases, the conductor 806 includes a substantially-straight region 812 that can be used to pull the one or more pre-formed relief sections of the conductor 806 through the conductor lumen 804. In at least some embodiments, when the conductor 806 is inserted into the lumen 804 the one or more pre-formed relief sections stretch out, as compared to the shape of the conductor 806 prior to insertion.

Figure 9A:
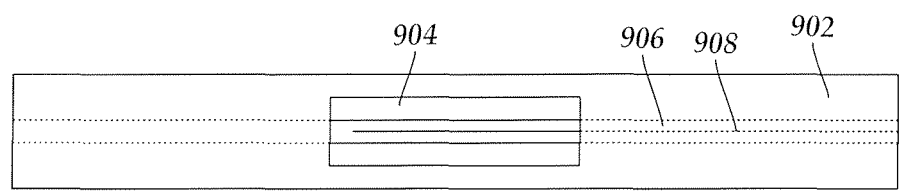
FIG. 9A is a schematic side view of one embodiment of a portion of a lead body with a removed section exposing an end portion of a conductor disposed in a lumen defined in the lead body, according to the invention.
Figure 9B:
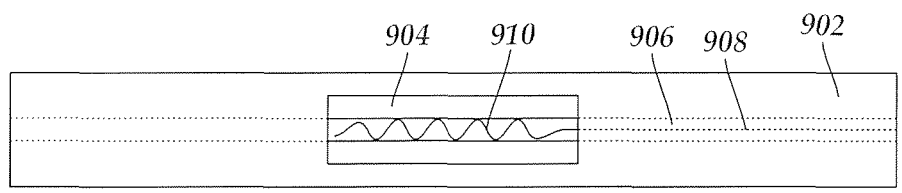
FIG. 9B is a schematic side view of one embodiment of the portion of the lead body with the removed section and the conductor of FIG. 9A with a relief section formed along a portion of the conductor exposed through the removed section, according to the invention.
Figure 9C:
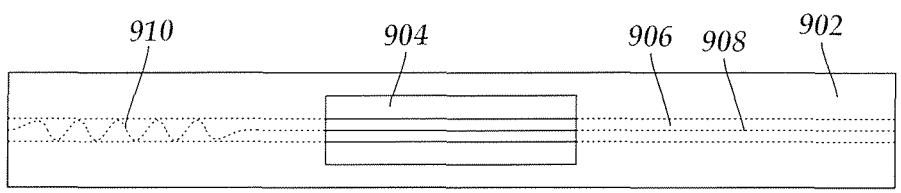
FIG. 9C is a schematic side view of one embodiment of the portion of the lead body with the removed section and the conductor of FIG. 9A with the relief section of FIG. 9B, the conductor threaded along a lumen of the lead body such that the relief section is not exposed through the removed section of the lead body, according to the invention.

Turning to FIGS. 9A-9C, in some embodiments strain relief is provided by forming one or more relief sections along the conductors during, or after, insertion of the conductors into the lead body. FIG. 9A is a schematic top view of one embodiment of a portion of a lead body 902 with an access aperture 904 (e.g., a removed section of the lead body 902) disposed along a length of the lead body 902. The access aperture 904 exposes a portion of a conductor lumen 906 extending along the lead body 902. A conductor 908 is inserted into the conductor lumen 906 and is partially threaded along the conductor lumen 906 such that the conductor 908 extends at least partially across the access aperture 904.

The portion of the conductor 908 extending at least partially across the access aperture 904 can be accessed through the access aperture 904 so that one or more relief sections can be formed along the conductor 908. FIG. 9B is a schematic top view of a relief section 910 formed along the conductor 908. Optionally, a plurality of relief sections 910 can be formed along the conductor 908. In at least some cases, the access aperture 904 may be sealed once the one or more relief sections 910 are formed.

In some cases, once the relief section 910 is formed, the conductor 908 can be threaded farther along the conductor lumen 906. FIG. 9C is a schematic top view of one embodiment of the conductor 908 threaded farther along the conductor lumen 906 such that the relief section 910 is no longer exposed through the removed section 904 of the lead body 902.

Any suitable number of access apertures 904 can be formed in the lead body 902. The access apertures 904 can be formed at any suitable location along the length of the lead body 902. In some cases, the access apertures 904 are formed in proximity to one (or both) of the ends of the lead body 902 (e.g., where the terminals or the electrodes are coupled to the lead body 902). In at least some embodiments, when the lead is inserted into the patient with a portion of the lead held in position by a retaining feature (see e.g., 210 in FIG. 2A), one or more of the access apertures 904 are located along the length of the lead body 902 such that at least one relief section 910 is disposed at a location that is in proximal proximity to the retaining feature.

Figure 10:
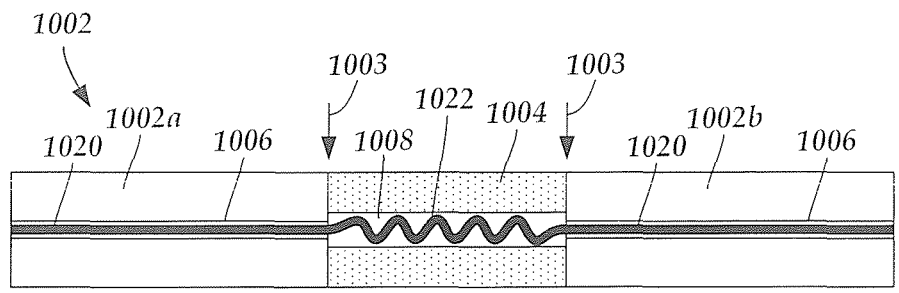
FIG. 10 is a schematic longitudinal cross-sectional view of one embodiment of a conductor with a strain relief section, the conductor disposed in a portion of a lead body that includes a spacer section disposed between two lead body portions, the conductor disposed in conductor lumens defined in each of the lead body portions with the relief section disposed in a strain relief cavity defined in the spacer section, according to the invention.

Turning to FIG. 10, in some cases one or more spacer sections can be disposed between lead body portions. In which case, strain relief can be provided by disposing one or more relief sections of the conductors within one or more strain relief cavities defined in the one or more spacer sections. The spacer sections can be formed in any suitable manner. In at least some embodiments, the spacer sections have outer diameters that are equal to outer diameters of the lead body portions. The lead body portions can be formed using pre-formed lead bodies of desired lengths. In at least some embodiments, the lead body portions are formed by severing a pre-formed lead body at a desired location along a length of the lead body to create desired lengths. The spacer section(s) can be coupled to the lead body portions using any suitable technique, such as reflowing the lead body portions and spacer.

FIG. 10 is a schematic longitudinal cross-sectional view of one embodiment of a portion of a lead body 1002. The lead body 1002 includes two lead body portions 1002a and 1002b flanking a spacer section 1004. The lead body portions 1002a, b each have an end configured and arranged for coupling to the spacer section 1004, indicated in FIG. 10 by arrows 1003. The lead body portions 1002a, b each define a conductor lumen 1006 extending along longitudinal lengths of the two lead body portions 1002a and 1002b. The spacer section 1004 defines a strain relief cavity 1008 extending along a longitudinal length of the spacer section 1004. The strain relief cavity 1008 is positioned in the spacer section 1004 with the strain relief cavity 1008 aligned with the conductor lumens 1006 along both ends of the strain relief cavity 1008 such that the strain relief cavity 1008 is in communication with the conductor lumens 1006 along both of the lead body portions 1002a and 1002b.

The strain relief cavity 1008 is configured and arranged to provide space for any suitable number of relief sections disposed along any suitable number of conductors. Any suitable number of conductor lumens 1006 may be in communication with the strain relief cavity 1008. In FIG. 10, a single conductor 1020 is shown extending along the conductor lumen 1006 and the strain relief cavity 1008. The conductor 1020 includes a single relief section 1022 disposed in the strain relief cavity 1008.

The relief section 1022 can be positioned in the strain relief cavity 1008 in any suitable manner. In one embodiment, the conductor 1020 is threaded through the lead portion 1002a. The relief section 1022 is formed along the portion of the conductor 1020 external to the lead portion 1002a in proximity to the connecting end of the lead portion 1002a. The spacer section 1004 is threaded over the conductor 1020 until one end of the spacer section 1004 abuts the end 103 of the lead portion 1002a and the strain relief cavity 1008 is disposed around the relief section 1022. The lead portion 1002b is then threaded over the conductor 1020 until the end 103 of the lead portion 1002b abuts the spacer section 1004. The spacer section 1004 may then be coupled to the lead portions 1002a and 1002b.

The strain relief cavity 1008 can have any suitable length and diameter. In at least some embodiments, the strain relief cavity 1008 has a diameter that is larger than a diameter of the one or more conductor lumens 1006 in communication with the strain relief cavity 1008. Any suitable number of strain relief cavities 1008 may be defined in a given spacer section 1004. When multiple strain relief cavities 1008 are disposed on a single spacer section 1004, in some cases at least one of the multiple strain relief cavities 1008 is configured and arranged to receive one or more relief sections 1022 of a single conductor. When multiple strain relief cavities 1008 are disposed on a single spacer section 1004, in some cases at least one of the multiple strain relief cavities 1008 is configured and arranged to receive one or more relief sections 1022 of a plurality of conductors 1020.

Any suitable number of spacer sections 1004 may be disposed along the lead body 1002 including, for example, one, two, three four, five, or more spacer sections 1004. In FIG. 10, a single spacer section 1004 is shown. The one or more spacer sections 1004 can be disposed at any suitable location along a length of the lead body 1002. In at least some embodiments, one or more of the spacer sections 1004 are disposed in proximity to a distal end of the lead body 1002. In at least some embodiments, when the lead is inserted into the patient with a portion of the lead held in position by a retaining feature (see e.g., 210 in FIG. 2A), one or more of the spacer sections 1004 are disposed at a location that is in proximal proximity to the retaining feature.

Figure 11:
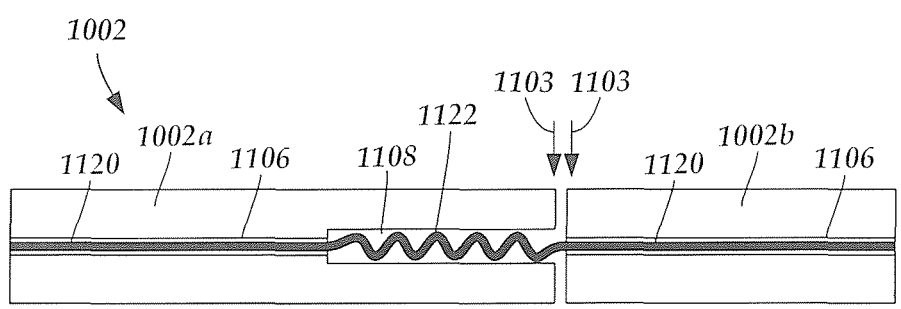
FIG. 11 is a schematic longitudinal cross-sectional view of one embodiment of a conductor with a strain relief section, the conductor disposed in a section of a lead body that includes two lead body portions, the conductor disposed in conductor lumens defined in each of the lead body portions with the relief section disposed in a strain relief cavity defined along a portion of one of the lead body portions, according to the invention.

In some cases, a strain relief cavity can be formed at one of the ends 103 of at least one of the lead body portions in addition to, or in lieu of, splicing in a spacer section. FIG. 11 is a schematic longitudinal cross-sectional view of one embodiment of a portion of the lead body 1102 having two lead body portions 1002a and 1002b each configured and arranged to couple with one another along corresponding connecting ends, indicated in FIG. 11 by arrows 1003. The lead body portions 1102a, b each define a conductor lumen 1106. A strain relief cavity 1108 is defined along the lead body portion 1002a at the connecting end 103. The strain relief cavity 1108 is aligned with the conductor lumen 1106 along both ends of the strain relief cavity 1108 such that the strain relief cavity 1108 is in communication with the conductor lumen 1106 at both ends of the strain relief cavity 1108.

The strain relief cavity 1108 is configured and arranged to provide space for one or more relief sections of one or more conductors extending along the one or more conductor lumens 1106 in communication with the strain relief cavity 1108. In FIG. 11, a single conductor 1120 is shown extending along the conductor lumen 1106 and the strain relief cavity 1108. The conductor 1120 includes a single relief section 1122 disposed in the strain relief cavity 1108. The strain relief cavity 1108 can have any suitable length and diameter. In at least some embodiments, the strain relief cavity 1108 has a diameter that is larger than a diameter of the one or more conductor lumens 1106 in communication with the strain relief cavity 1108.

Any suitable number of strain relief cavities 1108 may be disposed along the lead body 1102 including, for example, one, two, three four, five, or more strain relief cavities 1108. In FIG. 11, a single strain relief cavity 1108 is shown. The one or more strain relief cavities 1108 can be disposed at any suitable location along a length of the lead body 1102. In at least some embodiments, one or more of the strain relief cavities 1108 are disposed in proximity to a distal end of the lead body 1102. In at least some embodiments, when the lead is inserted into the patient with a portion of the lead held in position by a retaining feature (see e.g., 210 in FIG. 2A), one or more of the strain relief cavities 1108 are disposed at a location that is in proximal proximity to the retaining feature.

Figure 12:
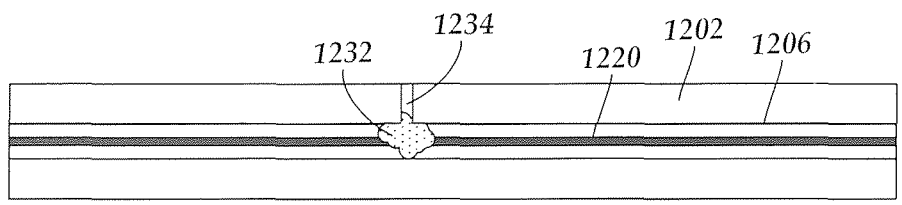
FIG. 12 is a schematic longitudinal cross-sectional view of one embodiment of a conductor extending along a lumen defined along a portion of a lead body that includes a fixation attachment fixedly coupling a portion of the conductor to the lumen, according to the invention.

Turning to FIG. 12, in some cases strain relief may be provided by fixedly attaching one or more of the conductors to the lead body at one or more locations along the length of the lead body. As disclosed above with reference to FIGS. 2A-3, bending of one portion of the lead may cause a corresponding undesired deflection at another portion of the lead due, at least in part, to stretching of the conductors. Fixedly attaching one or more of the conductors to the lead body at one or more locations along the length of the lead(s) may reduce the length of conductor spans along which a conductor can deflect in response to stretching. Thus, deflection may be localized and not extend to an end of the lead. Additionally, localizing a plurality of deflections may also reduce the magnitude of any single deflection. For example, fixedly attaching a conductor to a lead body at one or more locations between the intermediate portion and the distal portion of the lead may reduce the amount of (or even prevent) deflection at the distal portion of the lead caused by stretching of the conductor at an intermediate portion of the lead.

FIG. 12 is a schematic longitudinal cross-sectional view of one embodiment of a portion of a lead body 1202. A conductor 1220 extends along a conductor lumen 1206 defined in the lead body 1202. The conductor 1220 is attached to the conductor lumen 1206 at a fixation attachment 1232 disposed at a desired location along a length of the lead body 1202. The fixation attachment 1232 can be made using any suitable fixation technique including, for example, reflowing, injecting adhesive, or the like. In some cases, an access aperture 1234 may be formed in the lead body 1202 to provide access to the conductor lumen 1206 from a location external to the lead body 1202.

Any suitable number of fixation attachments 1232 may be disposed along the lead body 1202 including, for example, one, two, three four, five, or more fixation attachments 1232. In FIG. 12, a single fixation attachment 1232 is shown. The one or more fixation attachments 1232 can be disposed at any suitable location along a length of the lead body 1202. In at least some embodiments, one or more of the fixation attachments 1232 are disposed in proximity to a distal end of the lead body 1202. In at least some embodiments, when the lead is inserted into the patient with a portion of the lead held in position by a retaining feature (see e.g., 210 in FIG. 2A), one or more of the fixation attachments 1232 are disposed at a location that is in proximal proximity to the retaining feature.

Figure 13A:
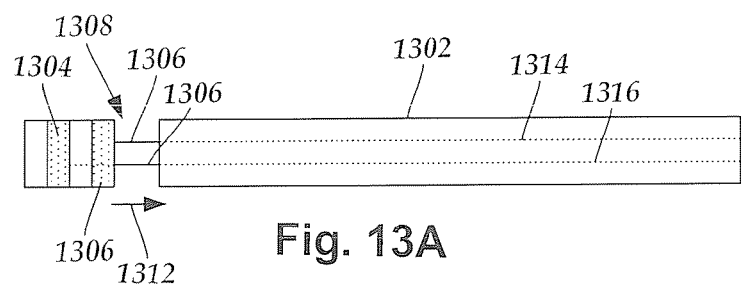
FIG. 13A is a schematic side view of one embodiment of a portion of a lead body that includes conductors extending along the lead body and coupled to contacts disposed at one end of the lead body, the lead body and the contacts separated from one another by a gap, according to the invention.

Turning to FIG. 13A, in some cases strain relief is provided by coupling the electrodes and terminals to opposing ends of the lead body such that gaps are formed at one (or both) of the ends of the lead body, electrically coupling conductors extending along the lead body to the electrodes and terminals, then pushing one (or both) of the electrodes and terminals into the lead body to eliminate the gap(s), thereby forming one or more relief sections in the conductors.

FIG. 13A is a schematic side view of one embodiment of a portion of one end of a lead body 1302. Contacts (e.g., electrodes or terminals) 1304 and 1306 are disposed at one end of the lead body 1302 and are electrically coupled to conductors 1314 and 1316, respectively, which extend along the lead body 1302. In some cases, the conductors 1314 and 1316 may extend to contacts disposed at an opposing end of the lead body 1302. Two conductors and two contacts are shown in FIG. 13A for exemplary purposes only. Any suitable number of conductors and contacts can be disposed in the lead body 1302.

Figure 13B:
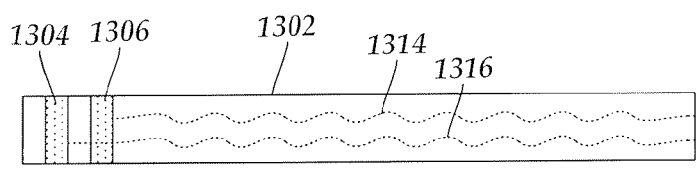
FIG. 13B is a schematic side view of one embodiment of the lead body of FIG. 13A and the contacts of FIG. 13A disposed at one end of the lead body, the contacts and the lead body pushed together to eliminate the gap of FIG. 13A formed between the lead body and the contacts, the elimination of the gap causing the conductors to form one or more relief sections, according to the invention.

A gap 1308 is formed between the lead body 1302 and the contacts 1304 and 1306. Once the contacts 1304 and 1306 are electrically coupled to the conductors 1314 and 1316, respectively, the contacts 1304 and 1306 can be pushed towards the lead body 1302, as shown by arrow 1312, to reduce (or eliminate) the gap 1308, as shown in FIG. 13B. It will be understood that, alternately (or additionally), the lead body 1302 can be pushed towards the contacts 1304 and 1306. Reducing, (or eliminating) the gap 1308 forms one or more relief sections along in the conductors 1306, which may create strain relief. Note that this technique can be used on either end, or both ends, of the lead body 1302.

Figure 14A:
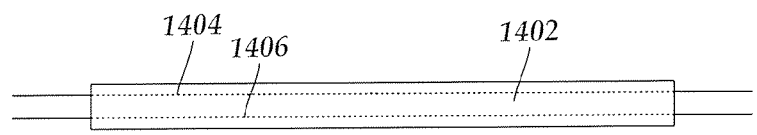
FIG. 14A is a schematic side view of one embodiment of two conductors extending along a lead body that is in a relaxed state, according to the invention.
Figure 14B:
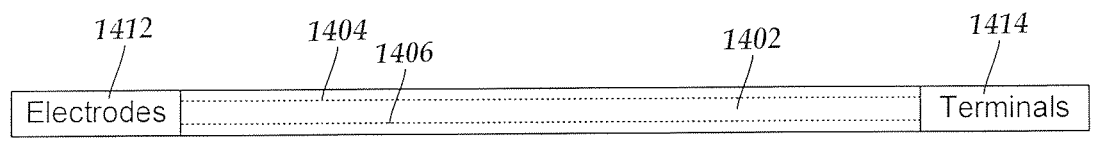
FIG. 14B is a schematic side view of one embodiment of the two conductors of FIG. 14A extending along the lead body of FIG. 14A while the lead body is in a stretched state, the two conductors coupled to electrodes disposed at one end of the stretched lead body and to terminals disposed at an opposing end of the stretched lead body, according to the invention.
Figure 14C:
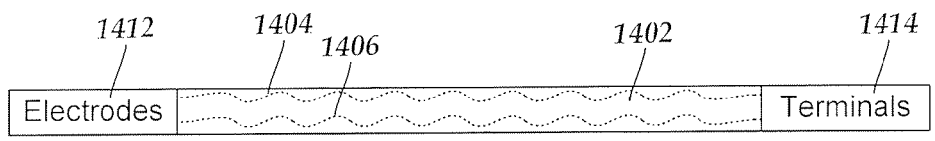
FIG. 14C is a schematic side view of one embodiment of the two conductors of FIG. 14A extending along the lead body of FIG. 14A while the lead body has returned to a relaxed state, the relaxation of the lead body causing the two conductors to each form one or more relief sections, according to the invention.

Turning to FIG. 14A-14C, in some cases strain relief is provided by longitudinally stretching the lead body, disposing conductors along the length of the lead body, attaching contacts (e.g., electrodes or terminals) to the ends of the lead body, coupling the ends of the conductors to the contacts, and allowing the lead body to relax, thereby forming one or more relief sections along the conductors.

FIG. 14A is a schematic side view of one embodiment of a lead body 1402 in a relaxed state. Two conductors 1404 and 1406 are shown extending along a longitudinal length of the lead body 1402. Two conductors are shown in FIG. 14A for exemplary purposes only. Any suitable number of conductors can be disposed in the lead body 1402.

FIG. 14B is a schematic side view of one embodiment of the lead body 1402 stretched along the longitudinal length of the lead body 1402. A plurality of electrodes 1412 are disposed at one end of the stretched lead body 1402, and a plurality of terminals 1414 are disposed at an opposing end of the stretched lead body. The conductors 1404 and 1406 are electrically coupled to the electrodes 1412 and the terminals 1414.

At some point after the conductors are electrically coupled to the electrodes and the terminals, the lead body is allowed to relax. FIG. 14C is a schematic side view of one embodiment of the electrodes 1412 and the terminals 1414 coupled to the lead body 1402 after the lead body 1402 has returned to a relaxed state. As the lead body 1402 relaxes, slack may form along the conductors, thereby forming one or more relief sections for providing strain relief.

In some cases, strain relief may be provided by increasing clearance between conductors and the conductor lumens within which the conductors extend. Clearance can be increased by increasing the diameter of the conductor lumens, decreasing the diameter of the conductors, or both. In at least some embodiments, the clearance is increased by decreasing the diameters of the conductors, as compared to conductors of at least some conventional leads. In at least one known lead, the conductor lumens have diameters of 0.01 inches (approximately 0.03 cm) and the conductors that extend within those conductor lumens have diameters of 0.007 inches (approximately 0.02 cm), thus providing a nominal clearance (e.g., half the difference between the diameters of the conductors and the diameters of the conductor lumens) of 0.0015 (approximately 0.004 cm) around the conductors.

In at least some embodiments, the conductor of the present invention has a nominal clearance of at least 0.002 inches (approximately 0.005 cm), 0.0025 inches (approximately 0.006 cm), 0.003 inches (approximately 0.008 cm), 0.0035 inches (approximately 0.009 cm), 0.004 inches (approximately 0.01 cm) or more. In some embodiments, the conductor of the present invention is 1 ×7 filar. In other embodiments, the conductor of the present invention is 1×3 filar. In some embodiments, the conductor of the present invention has a diameter that is no greater than 0.005 inches (approximately 0.01 cm), 0.004 inches (approximately 0.009 cm), or 0.003 inches (approximately 0.008 cm).

In addition to increasing clearance, decreasing the diameter of the conductor may also have the advantage of increasing flexibility of the conductor. Increased flexibility of the conductor may cause the lead to exert a lower amount of force and deflect less when a force is applied to the lead (see e.g., FIG. 3). Additionally, increasing the flexibility of the conductor may enable the conductor to exert a lower force when biased and disposed in conductor lumen, thereby potentially resulting in reduced distortion of the conductor lumens and, consequently, the overall lead body.

In some cases, insulation may be disposed around the conductor of the present invention. The insulation may be coated with one or more materials which enable the conductors to slide relative to the lumens within which the conductors are disposed. In at least some embodiments, strain relief is provided by coating insulation disposed around the conductor with one or more materials that provide outer surfaces of the insulation with a lower coefficient of friction than ethylene tetrafluoroethylene. Examples of such materials include perfluoroalkoxy polymers ("PFA"), polytetrafluoroethylene ("PTFE"), or the like.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for manufacturing a lead, the method comprising:
    inserting a conductor into a conductor lumen defined along a length of an elongated lead body, the lead body having a first end and an opposing second end, wherein the conductor lumen defines a plurality of helical sections separated from one another by straight, wherein each of the helical sections is arranged in counterrotaion to adjacent ones of the plurality of helical sections;
    disposing a first conductive contact at the first end of the lead body with a first gap formed between the first conductive contact and the first end of the lead body;
    electrically coupling the first end of the conductor to the first conductive contact;
    disposing a second conductive contact at the second end of the lead body;
    electrically coupling the second end of the conductor to the second conductive contact; and
    reducing the first gap between the first conductive contact and the first end of the lead body, wherein reducing the first gap causes the conductor to form at least one first relief section.

2. The method of claim 1, wherein disposing a second conductive contact at the second end of the lead body comprises disposing the second conductive contact at the second end of the lead body with a second gap formed between the second conductive contact and the second end of the lead body.

3. The method of claim 1, wherein the first conductive contact is a terminal and the second conductive contact is an electrode.

4. The method of claim 1, wherein the first conductive contact is an electrode and the second conductive contact is a terminal.

5. The method of claim 1, wherein the first conductive contact is either an electrode or a terminal and the second conductive contact is a terminal when the first conductive contact is the electrode and the second conductive contact is an electrode when the first conductive contact is the terminal.

6. A method for manufacturing a lead, the method comprising:
    inserting a conductor into a conductor lumen defined along a length of an elongated lead body, the lead body having a first end and an opposing second end;
    disposing a first conductive contact at the first end of the lead body with a first gap formed between the first conductive contact and the first end of the lead body;
    electrically coupling the first end of the conductor to the first conductive contact;
    disposing a second conductive contact at the second end of the lead body with a second gap formed between the second conductive contact and the second end of the lead body;
    electrically coupling the second end of the conductor to the second conductive contact;
    reducing the first gap between the first conductive contact and the first end of the lead body, wherein reducing the first gap causes the conductor to form at least one first relief section; and
    reducing the second gap between the second conductive contact and the second end of the lead body, wherein reducing the second gap causes the conductor to form at least one second relief section.

7. The method of claim 6, wherein the conductor lumen defines at least one helical section.

8. The method of claim 7, wherein the conductor lumen defines a plurality of the helical sections separated from one another by straight sections.

9. The method of claim 8, wherein each of the helical sections is arranged in counterrotation to adjacent ones of the plurality of helical sections.

10. The method of claim 7, wherein the conductor lumen defines a plurality of the helical sections and at least one of the helical sections is arranged in a clockwise configuration and at least one of the helical sections is arranged in a counterclockwise configuration.

11. The method of claim 7, wherein the conductor lumen defines a plurality of the helical sections and each of the helical sections has a length that is different from at least one other of the plurality of helical sections.

12. A method for manufacturing a lead, the method comprising:
   inserting a conductor into a conductor lumen defined along a length of an elongated lead body, the lead body having a first end and an opposing second end, wherein the conductor lumen defines a plurality of helical sections, wherein each of the helical sections has a length that is different from at least one other of the plurality of helical sections;
   disposing a first conductive contact at the first end of the lead body with a first gap formed between the first conductive contact and the first end of the lead body;
   electrically coupling the first end of the conductor to the first conductive contact;
   disposing a second conductive contact at the second end of the lead body;
   electrically coupling the second end of the conductor to the second conductive contact; and
   reducing the first gap between the first conductive contact and the first end of the lead body, wherein reducing the first gap causes the conductor to form at least one first relief section.

13. The method of claim 12, wherein the conductor lumen defines the plurality of the helical sections separated from one another by straight sections.

14. The method of claim 13, wherein each of the helical sections is arranged in counterrotation to adjacent ones of the plurality of helical sections.

15. The method of claim 12, wherein at least one of the helical sections is arranged in a clockwise configuration and at least one of the helical sections is arranged in a counterclockwise configuration.

* * * * *